United States Patent [19]

Chen

[11] Patent Number: 6,124,497
[45] Date of Patent: Sep. 26, 2000

[54] PREPARATION OF ALKANE SULFONIC ACIDS AND SULFONYL CHLORIDES BY OXIDATION OF ALKANETHIOLS AND DIALKYL DISULFIDES

[75] Inventor: Johnson Chen, King of Prussia, Pa.

[73] Assignee: Innochem Inc., Phoenixville, Pa.

[21] Appl. No.: 09/367,297

[22] PCT Filed: Dec. 23, 1997

[86] PCT No.: PCT/US97/23723

§ 371 Date: Oct. 22, 1999

§ 102(e) Date: Oct. 22, 1999

[87] PCT Pub. No.: WO98/34914

PCT Pub. Date: Aug. 13, 1998

Related U.S. Application Data

[63] Continuation of application No. 08/797,343, Feb. 10, 1997, abandoned.

[51] Int. Cl.$^7$ .................................................. C07C 303/16
[52] U.S. Cl. ........................... 562/118; 562/828; 562/829
[58] Field of Search ....................................... 562/828, 829, 562/118

[56] References Cited

U.S. PATENT DOCUMENTS 3,993,692  11/1976  Giolito .................................... 562/828

*Primary Examiner*—Robert Gerstl
*Attorney, Agent, or Firm*—Fay, Sharpe, Fagan, Minnich & McKee, LLP

[57] ABSTRACT

A process for preparing alkane sulfonic acids and sulfonyl chlorides by oxidation of alkanethiols or dialkyl disulfides in the presence of nitric acid or nitric oxides as a catalyst and in the presence of bromide as a cocatalyst.

22 Claims, No Drawings

PREPARATION OF ALKANE SULFONIC ACIDS AND SULFONYL CHLORIDES BY OXIDATION OF ALKANETHIOLS AND DIALKYL DISULFIDES

This application is a 371 of PCT/US97/23723 filed Dec. 23, 1997 and a continuation of Ser. No. 08/797,343 filed Feb. 10, 1997 now abandoned.

FIELD OF THE INVENTION

The invention relates to the manufacture of alkane sulfonic acids and sulfonyl chlorides by oxidation of the corresponding alkanethiol or dialkyl disulfide. More specifically, it relates to the oxidation of such compounds, in the presence of nitric acid or a nitrogen oxide and $Br_2$ or HBr, to form the corresponding sulfonic acids or sulfonyl chlorides.

BACKGROUND OF THE INVENTION

Alkylsulfonic acids (or alkane sulfonic acids) and alkyl sulfonyl chlorides are well known large scale commercial products useful as surfactants and as chemical intermediates among other applications. Thus it is desirable to prepare them by a highly efficient process which results in no or a minimum of by-products and which is environmentally sound. The process of this invention provides such a synthesis.

DISCUSSION OF THE PRIOR ART

Numerous methods have been used previously to prepare alkyl sulfonic acids from alkylthiols and disulfides. However, these methods tend to be uneconomic, or to result in the production of unwanted side products. The most commonly used method for the manufacture of alkane sulfonic acids involves oxidation of the corresponding alkanethiol or dialkyl disulfide by chlorine in concentrated hydrochloric acid media, as disclosed, for example, in U.S. Pat. No. 3,630,004 to Adair, et al. and U.S. Pat. No. 4,280,966 to Hübenett. This method suffers from the disadvantage that a significant amount of side products is formed. The side product results from the side chain chlorination of the alkyl group, particularly in the case of higher alkane sulfonic acids. A large amount of hydrochloric acid is also formed as a by-product of the oxidation reaction which presents a disposal problem. In addition, side products result from the side chain chlorination of the alkyl chain of the alkanethiol or disulfide and this is a concern, particularly in the case of higher alkane sulfonic acids.

Oxidation of aliphatic thiols and disulfides to the corresponding sulfonic acid by heating in an excess of is dimethyl sulfoxide, with a catalytic amount of bromine, iodine or hydrogen iodide as a secondary catalyst, is disclosed in U.S. Pat. No. 3,948,922 to Lowe. Oxidation of the sulfide-sulfur bond-containing compounds by lower dialkyl sulfoxides, promoted by bromide ion, is described in U.S. Pat. No. 3,428,671 to Toland. Oxidation of thiols to disulfides by their reaction with a lower alkyl sulfoxide in the presence of a catalyst consisting of chlorine or hydrogen chloride as the primary catalyst and iodine or hydrogen iodide as a secondary catalyst is disclosed in U.S. Pat. No. 3,954,800 to Lowe. In these processes using dimethyl sulfoxide as the oxidizing agent, this agent is consumed in stoichiometric amounts. In view of the high cost of dimethyl sulfoxide, such a process is uneconomic. Further, because of the intense odor of the dimethyl sulfide formed, the process may cause difficult environmental problems.

More recently, European Patent Application Publication No. 4,424,616 A2 discloses that alkanethiol and dialkyl sulfides may be converted to alkyl sulfonic acids with oxygen and a catalytic amount of a lower dialkyl sulfoxide using water and a hydrogen halide (e.g., HI, HBr and their mixtures). Yields for the reaction, however, are quite low.

Proell, et al., U.S. Pat. No. 2,433,395, disclose that alkyl mercaptans and alkyl disulfides may be converted to alkyl sulfonic acids in an aqueous system using oxygen and a nitrogen oxide. However, the oxidation is incomplete and the process is not commercially viable.

U.S. Pat. No. 2,697,722 to Johnson, et al. discloses the aqueous oxidation of alkyl disulfides with oxygen, but the process does not employ the co-catalyst of this invention.

The conversion of alkane thiols and disulfides to alkyl sulfonyl chlorides by use of chlorine and HCl is also known. However, this process also suffers from the same disadvantage of producing large amounts of hydrochloric acid as co-product. The side chain chlorination of the alkyl chain is also a concern with this reaction, especially in the case of higher alkyl sulfonyl chlorides.

Chemical Abstracts, Vol. 71, 1969, p. 123569 discloses the use of aqueous HCl in a tubular reactor to convert an alkane thiol or disulfide to the corresponding sulfonyl chloride.

Similarly, Chemical Abstracts, Vol. 111, 1989, p. 136438s, discloses the conversion of alkane thiol and disulfides to the sulfonyl chloride by use of aqueous HCl using hydrogen peroxide as an oxidizing agent. The high cost of hydrogen peroxide renders this process uneconomical.

The disclosure of Chemical Abstracts, Vol. 112, 1990, p. 65465f, shows the preparation of alkane sulfonyl halides by electrolysis of the thiol or disulfide in aqueous HCl solution. However, because of the extremely high cost of the electrolytic equipment, this process is not an economically viable one.

SUMMARY OF THE INVENTION

In accordance with one embodiment of the present invention, a process for preparing an alkane sulfonic acid or sulfonyl chloride is provided. An alkanethiol, a dialkyl disulfide or a mixture thereof is contacted in an aqueous medium with an oxygen-containing gas in the presence of catalytic amounts of nitric acid or a nitrogen oxide together with $Br_2$ or HBr as a co-catalyst to produce the corresponding alkane sulfonic acid. When preparing the alkane sulfonyl chloride, the reaction medium will also contain hydrogen chloride.

In accordance with another embodiment of the present invention, a process for the preparation of alkane sulfonic acids or alkane sulfonyl chlorides of a formula $R_1$—$SO_2$—Y where $R_1$ is an alkyl group of from 1 to about 18 carbon atoms and Y is —OH or —Cl is provided. The process comprises oxidizing a sulfur compound of the formula $R_1SZ$, where Z is —H or —$SR_1$. The oxidation occurs in aqueous phase in the presence of nitric acid and bromine and, where a sulfonyl chloride product is desired, in the presence of HCl.

By careful selection of the reaction parameters, the reaction yields the alkane sulfonic acid or sulfonyl chloride cleanly and quickly, and the product is easily separated from the reaction mixture. In addition, no unwanted by-products are generated and the process is environmentally desirable. Products with a sulfuric acid content within the accepted industry standard of 350ppm are readily obtained.

DETAILED DESCRIPTION OF THE INVENTION

It has now been found that a highly efficient process for producing alkane sulfonic acids from an alkyl sulfur compound selected from the group of alkylmercaptans and dialkyl disulfides is achieved by employing oxygen, an oxygen-containing gas, or nitric acid as an oxidant, nitric acid or nitrogen oxides as a catalyst, and hydrogen bromide or bromine as a co-catalyst. The process is carried out in the presence of water, and where a sulfonyl chloride product is desired, HCl is added to the aqueous phase reaction mass. While either bromine or HBr may be used as co-catalyst, it is preferred to use HBr for economic reasons and because it is easier to handle. Thus, compounds prepared by the process of the invention will have the chemical formula $R_1$—$SO_2$—Y where $R_1$ is an alkyl group of from 1 to about 18 carbon atoms and Y is —OH or —Cl. The starting sulfur-containing compounds will be of the formula $R_1SZ$ where $R_1$ is defined above Z is —H or —SR $._1$ Typical starting materials are the alkyl thiols and disulfides such as methanethiol, ethanethiol, isopropanethiol, butanethiols, hexanethiols, 1-decanethiol, 1-dodecanethiol, 1-hexadecanethiol, dimethyl disulfide, diethyl disulfide, dipropyl disulfide, dodecyl disulfide, and the like. The $R_1$ groups on the disulfides may be the same or different. When lower alkyl sulfonic acids and sulfonyl chlorides are to be prepared, it is preferred to use a disulfide because the lower alkylthiols are foul smelling and more difficult to handle. The process of the invention produces high yields and provides easy separation of the desired product.

While not wanting to be bound by any theory, it is believed that the following chemical equations illustrate the overall process of the invention:

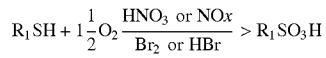

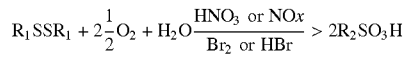

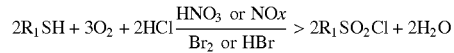

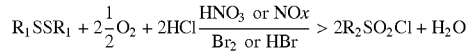

The nitrogen oxides (NOx) active as catalysts in the reaction are those where x is an integer of 1 or 2 and it is believed that such nitrogen oxides are formed by the decomposition of the nitric acid used as catalyst.

In the preparation of a sulfonyl chloride, one mole of HCl per mole of the sulfur reactant is the stoichiometric amount. Use of more than one mole will result in excess HCl in the reaction mass and, preferably, no more than about 5 moles of HCl per mole of the sulfur reactant should be used.

The amount of water in the aqueous reaction system is not critical, but for ease of product separation, an amount of water is used which will give a product concentration in the aqueous system of from about 20% to about 90%.

According to equations III and IV, it can be seen that the yield of sulfonyl chloride can be increased by decreasing the water content while increasing the HCl content in the reaction medium to drive the reaction to completion. It is conceivable that the maximum yield of sulfonyl chloride can be achieved by using anhydrous conditions, whereby no hydrolysis of sulfonyl chloride to sulfonic acid can take place.

Equations I through IV summarize the overall reaction. The chemistry of the process, however has been found to be more complex than the above equations express. The process is believed to involve gas-liquid phase changes between the reactants and products. For example, nitric acid, a liquid, reacts to form nitric oxide (NO), a gas, which reacts with oxygen to form nitrogen dioxide ($NO_2$). The gaseous nitrogen dioxide in turn reacts with water to form nitric acid. The reaction can be described in the following steps:

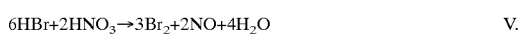     V.

     VI.

The sum of equations V. and VI. becomes

     VII.

The bromine formed in equation V. plays an active roll in the oxidation of alkyl mercaptan or alkyl disulfide to alkyl sulfonic acid as follows:

     VIII.

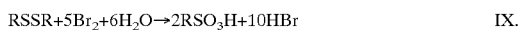     IX.

The time required for the phase changes between reactants and reaction products slows down the overall rate of the process. From equations V. and VI., it can be seen that phase changes take place between liquid nitric acid and gaseous nitric oxide and oxygen. The rate of regeneration of nitric acid is a function of the rate of dissolution of nitric oxide and oxygen, or their reaction product nitrogen dioxide, in water.

METHODS FOR PREPARING ALKYL SULFONIC ACID AND SULFONYL CHLORIDE

As discussed above, it is thought that bromine is responsible for the conversion of the sulfur compound to a sulfonic acid. For ease of handling, the bromine for the reaction is preferably generated from HBr, although it is also contemplated that bromine, rather than HBr be used as an initial starting material. This is readily achieved in one of two ways. In the first, oxygen is used to oxidize the HBr, in the presence of catalytic amounts of nitric acid. In the second, nitric acid, rather than oxygen is used as an oxidant. The methods can also be used for subsequent regeneration of bromine from HBr formed during the reaction. The nitric acid is preferably recovered for further oxidation of hydrogen bromide. In both methods of bromine generation, the result is a net consumption of oxygen.

I. PROCESS USING BROMINE

In this method, the reactants are all combined within the same reactor. It is thought that the bromine catalyst is regenerated from HBr throughout the process according to equation V. above. Reaction temperatures will vary somewhat depending on the particular product being made, and the process route selected. When preparing a sulfonyl chloride, the reaction temperature should be maintained at from about 0° C. to about 50° C.

II. PROCESS USING OXYGEN AS A BROMINE GENERATING AGENT

A. Single Reactor Process

In this method, the reactants are all combined within the same reactor. Oxygen is used in the generation, or regeneration, of bromine, in the presence of catalytic amounts of nitric acid. It is thought that the bromine catalyst is regenerated from HBr throughout the process according to equation V. above. Reaction temperatures will vary somewhat depending on the particular product being made, the process route selected, and whether HBr or $Br_2$ is used. When preparing alkane sulfonic acids with $Br_2$, the reaction may be started at room temperature (about 20° C.), but will self-initiate and rise to a temperature from about 80° C. to about 100° C. When using HBr to prepare alkane sulfonic acids, an initial heating to about 50° C. to about 80° C. is needed to initiate a reaction. When preparing a sulfonyl chloride, the reaction temperature should be maintained at from about 0° C. to about 50° C.

The amount of catalyst and co-catalyst used in the process is not critical, but will normally be in the range of from about 0.5% to about 50% of the weight of reactant sulfur compounds for nitric acid or nitrogen oxides, and from a trace amount to about 50% by weight of reactant sulfur compound for HBr or $Br_2$. The preferred amount for nitric acid or nitrogen oxides ranges from about 5% to about 25% of reactant sulfur compounds and from about 2% to about 25% of the weight of reactant material for $Br_2$ or HBr. In general, the amount of the catalyst used should be sufficient to effect a desirable reaction rate, but the amount used should not make separation of the product from the catalyst difficult.

The single reactor process provides an efficient method of preparation of sulfonic acids and chlorides. However, for some applications, the sulfuric acid content of the final product is higher than desirable (in the range 2500 ppm. to 1.5%). To meet the industry-accepted specification for purity, a sulfuric acid concentration of 350 ppm. or less is required. It is speculated that the sulfuric acid content of the alkyl sulfonic acid arises from the over-oxidation of the sulfur compound in the severe oxidation environment. By modifying the reaction conditions as explained below, a sulfuric acid concentration of 350 ppm. or less is readily achieved.

In addition, the rate of regeneration of nitric acid, and the overall reaction rate, are dependent on the rate of dissolution of nitric oxide and oxygen. This dissolution is less favorable at an elevated temperature under which the oxidation of the sulfur compound takes place. By modification of the reaction conditions to alter the location of the oxygen introduction as described below, the overall rate of reaction is increased significantly.

B. Two Reactor Process

To minimize the level of sulfate contamination in the reaction products, the reaction is preferably carried out in two steps. The two step process will be described with reference to the formation of alkyl sulfonic acids. It should be understood, however, that the method is also suited to the preparation of sulfonyl chlorides. The first step involves the oxidation of HBr to bromine ($Br_2$). The second step is the oxidation of a sulfur compound, such as dialkyl sulfide or alkyl mercaptan, to a sulfonic acid by the bromine.

In the first step of this method, HBr and catalytic amounts of nitric acid are combined in solution. Oxygen is introduced to generate bromine. The second-step oxidation of the sulfur compound is carried out without the interference of oxygen. Equations VIII. and IX. summarize likely reaction mechanisms for the second step. The first step is carried out in the absence of the more sensitive sulfur compound.

By repeating steps 1 and 2 sequentially, the concentration of the product alkyl sulfonic acid can be increased by timely additions of the sulfur compound and oxygen, without further addition of HBr, bromine, nitric acid or nitrogen oxide.

In the second-step oxidation, the introduction of the sulfur compound is preferably controlled at such a rate that no residue is left unreacted. In other words, there is always excess bromine in the reaction mixture in the second step. A brown color in the reaction mixture indicates the existence of excess bromine. When the first step is repeated, therefore, there is little or no sulfur compound remaining to be oxidized in the more severe oxidation conditions therein. Controlling the rate of addition of the sulfur compound in this way reduces the level of sulfuric acid in the sulfonic acid product to below 250 ppm., well within the industrial specification of 350 ppm. The two-step process thus likely avoids over-oxidation of the sulfur compound to sulfuric acid.

Preferably, the two steps of the process are carried out in separate reactors. The first reactor provides for the generation of bromine. The reaction mixture containing bromine is then transported to a second reactor, to which the disulfide or mercaptan is introduced to make sulfonic acid. Preferably, the reaction mixture, still containing a slight excess of bromine, is then transported back to the first reactor for bromine regeneration. In practice, a pump is used to circulate the reaction fluid between the two reactors. This two-reactor arrangement reduces the chance of direct contact of sulfur compound with the more severe oxidation conditions in the first reactor. The reaction material is transported back and forth between the two reactors, until a desirable level of alkyl sulfonic acid is accumulated. The reaction mixture containing alkyl sulfonic acid is then withdrawn from the reactor in part or in entirety and transported to a separation unit for the separation of sulfonic acid from the reaction mixture.

In general, the amount of HBr in the reaction mixture is not critical for the oxidation reaction. However, in order to maintain a meaningful reaction rate, at least a few percent of hydrogen bromide is necessary. When sulfuric acid contamination is an issue, it is beneficial to maintain higher concentrations of HBr. This ensures a a high concentration of bromine in the reaction mixture. The high concentration of bromine increases the likelihood that the sulfur compound will react with bromine rather than with nitric acid. This reduces the opportunity for the nitric acid to react with the sulfur compound in certain undesirable ways, producing a by-product, such as sulfuric acid. However, too much hydrogen bromide could cause unnecessary work in the final purification step, where the hydrogen bromide is removed from the product mixture. The optimum hydrogen bromide concentration is dependent on the particular reaction under consideration. In general, a desirable hydrobromic acid or hydrogen bromide solution concentration range is from as low as a fraction of 1 percent to about an equal molar ratio of the sulfur compound under consideration.

The reaction temperature is not of critical importance. In general, the rate of reaction is higher at a higher temperature. For convenience, the reaction temperature is optionally determined by the amount of reaction heat released from the oxidation of the sulfur compound in question. A temperature range of from about 50° C. to about the boiling point of the reaction mixture is generally preferred. Reaction temperatures below 50° C. could require cooling of the reaction mixture, depending on the heat generated in the reaction.

Using this method, sulfuric acid concentrations of less than 500 to 700 ppm. were achieved. When the rate of sulfur compound addition to the second reactor was controlled to maintain an excess of bromine, concentrations of below 250 ppm. sulfuric acid in a methane sulfonic acid product were achieved. This latter level of sulfuric acid is well within the industrial standard of 350 ppm. However, the reaction rate for this process is still limited by the rate of dissolution of the gaseous reactants. The following process eliminates the dependence on the rate of gaseous dissolution, which generally provides a significant improvement in the overall reaction rate.

III. PROCESS USING NITRIC ACID AS AN OXIDANT

In this method, nitric acid, rather than oxygen, is used as an oxidant to generate bromine from HBr. This method preferably uses a stoichiometric amount of nitric acid in relation to the amount of sulfur compound to be oxidized in the second step. However, the nitric acid is recovered quantitatively in the recovery unit. The net consumption of oxidant still is in the form of oxygen.

The chemistry of this process is represented by equations X and XI:

$$RSH + 2HNO_3 \xrightarrow{HBr} RSO_3H + H_2O + 2NO \qquad \text{X.}$$

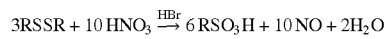
$$3RSSR + 10HNO_3 \xrightarrow{HBr} 6RSO_3H + 10NO + 2H_2O \qquad \text{XI.}$$

The nitric oxide produced is recycled to react with oxygen and water to regenerate nitric acid, as expressed in equation VI. This is preferably accomplished in a separate unit, operated at a significantly lower temperature, which greatly enhances the rate of nitric acid formation.

In practice, the process can be carried out with either one or two reactors. The one reactor and two reactor processes are illustrated below.

A. One Reactor Process

A catalytic amount of hydrobromic acid solution is charged into the reactor together with a small amount of nitric acid. The reactor is subjected to heat to initiate the formation of bromine. The sulfur compound is added to maintain the reaction. Once the reaction is under way, the heat can be reduced or removed. The temperature will vary according to the addition rate of the reactants. The reaction temperature is not generally critical. A temperature of between about 50° C. and the boiling point of the reaction mixture is preferred. Below 50° C., the reaction rate tends to be slower, or cooling of the reaction mixture may be required. The reaction rate of this process is generally significantly faster than the process described above using oxygen to generate the bromine. The nitric oxide produced is transported to a separate unit to regenerate nitric acid. The detail of the nitric acid regenerating device is well known to those who are skilled in the art.

Alternatively, the reactor is pre-charged with the desired amount of nitric acid, together with a catalytic amount of hydrobromic acid or hydrogen bromide. As soon as the mixture turns brown, usually without heat, the sulfur compound, such as alkyl mercaptan or alkyl disulfide, is added at such a rate that a gentle reaction is maintained until the calculated amount is added. Again, the nitric oxide is recovered as nitric acid in a separate unit.

The reaction temperature for the one-reactor process is usually higher than for other methods, because the single reactor has less surface area from which heat is lost.

The product mixture from the reaction process is then removed from the reactor for the separation of alkyl sulfonic acid from the rest of reaction components in a separate purification unit.

With proper process control, the concentration of sulfuric acid in the alkyl sulfonic acid product is contained within a desirable level, as evidenced by the Examples.

B. Two Reactor Process

This process is similar to the two-reactor process using oxygen as a bromine generator except in that nitric acid is used in the first reactor instead of oxygen. The two reactor process is particularly suited to the production of methane sulfonic acid from methyl mercaptan. The sulfonic acid product has a low sulfuric acid content.

In the first step, the first reactor is charged with a catalytic amount of aqueous hydrogen bromide or hydrobromic acid solution, together with nitric acid. Heat is applied to initiate the generation of bromine. In the second step, the bromine-laden mixture is transported to a second reactor to react with alkyl mercaptan or alkyl disulfide to produce alkyl sulfonic acid. The bromine depleted reaction mixture is then transferred back to the first reactor for further bromine generation. The reaction solution is transported back and forth until a desirable level of alkyl sulfonic acid is accumulated, which is then withdrawn for separation and purification. The nitric oxide produced is recovered as nitric acid in the nitric acid regeneration unit for subsequent reuse in generating bromine. When an alkyl sulfonic acid containing a low sulfuric acid concentration is desired, an excess amount of bromine is maintained in the reaction mixture to prevent over-oxidation of the sulfur compound by nitric acid. Methane sulfonic acid made by this route had a sulfuric acid impurity of less than 300 ppm.

IV. SEPARATION OF THE ALKYL SULFONIC ACID AND SULFONYL CHLORIDE PRODUCTS

Several methods can be employed to separate the alkyl sulfonic acid from the reaction mixture. In one method, the lower boiling point components are distilled off the mixture, leaving the sulfonic acid behind in the separation equipment. In another method, steam is employed to vaporize the lower boiling components from the mixture. Alternatively, vacuum distillation is used for the separation.

The crude sulfonic acid thus obtained still contains a trace amount of HBr, which is further reduced by treating the crude product with hydrogen peroxide. This converts the HBr to bromine. Since bromine does not form an azeotropic mixture with water and has a lower boiling point than HBr, it is readily separated from the sulfonic acid by heating or vacuum stripping the crude sulfonic acid to produce a colorless, odorless sulfonic acid. By careful control of the reaction conditions, the level of sulfuric acid impurity in the sulfonic acid produced in the two-step process is 300 ppm. or less, well within the accepted range of industrial specification.

Alkyl sulfonyl chloride products are not soluble in aqueous medium and are heavier than the corresponding sulfonic acids and, thus, they are easily separated from the reaction mixture by phase separation. The crude alkyl sulfonyl chloride is preferably further purified by washing with cold mild alkaline solutions, such as sodium bicarbonate solution. This removes the last traces of catalyst. The purified product is optionally further refined by distillation.

The following examples will illustrate the invention:

EXAMPLES

I. Using Bromine

EXAMPLE 1

Using Bromine for Preparation of MSA from DMDS

Laboratory preparation of both alkane sulfonic acids and alkyl sulfonyl chloride were carried out in the following equipment assembly:

A round bottom flask fitted with a magnetic stirrer was also fitted with two addition funnels, an addition tube extending below the surface of the reaction mass for oxygen gas addition, and a tube for exit of product gases which was connected to a scrubber device. The scrubber device consisted of two 250 ml. Erlenmeyer flasks connected in series and filled with a scrubbing fluid such as nitric acid, hydrogen peroxide, or a mixture of both which is effective to remove obnoxious product gases. In the following examples, the mixture of $HNO_3$ and $H_2O_2$ was used and the aqueous fluid volume was about 200 ml. The exit tube from the reactor flask entered the first Erlenmeyer flask from above the liquid level and the tube connecting the two flasks extended to the bottoms of both flasks. The second flask was open to the atmosphere. With this arrangement, when there was a pressure build up in the system, the fluid would flow from the first to the second flask, and when a negative pressure resulted, the flow of fluid would be in the opposite direction. During the course of the reaction, oxygen feed was controlled so that the scrubbing fluid movement was minimal.

Using the apparatus described above, the round bottom flask was charged with about 1 g. of $Br_2$ and 12.7 g. of water. One addition funnel was charged with 18.8 g. (0.2 moles) of DMDS and the other was charged with 1.04 g. of 68% nitric acid and 13.3 g. of water. The system was not purged with oxygen for fear of losing the bromine. Low heat was maintained throughout the entire process at about 55° C. to about 65° C. for two hours and 50 minutes.

Five drops of DMDS were added to the reaction flask. The reaction started with the immediate disappearance of the brown bromine color. After charging 0.95 g. of the nitric acid into the reactor flask, oxygen flow to the reaction mass was turned on and DMDS was dropped into the flask at a rate of five drops per interval of one to three minutes. The rate of reaction slowed down after 22 minutes and intermittent addition of nitric acid solution from the other addition funnel became necessary to maintain the reaction.

The addition of DMDS was completed in one hour and 40 minutes and the addition of nitric acid solution was completed in one hour and 50 minutes. After completing the addition of nitric acid solution, the reaction mass was held for another one hour at low heat. During this one hour period, the rate of oxygen flow was adjusted continuously to essentially equal the rate of oxygen absorption. The reaction mixture was deep brown in both liquid and gas phases. The product material in the reactor flask weighed 62.3 g. This was mixed with 40 g. of water and distilled to separate the $HNO_3$ and $Br_2$. During distillation, when the liquid temperature reached 140° C., an additional 8 ml. of water was added and distillation continued. This water addition was made three times. At the end of distillation, two drops of 50% hydrogen peroxide were applied to test for residual hydrogen bromide. This was shown to be absent by the lack of any brown color in the product mass. A total of 50.5 g. of material was recovered which contained 72.4% MSA; Sp. Gr. 1.37. The yield of MSA recovered was 95%. The total amount of the $HNO_3$ catalyst used was 7.2% of the weight of the DMDS and the amount of $Br_2$ co-catalyst was 5.3% of DMDS.

IA. Single Reactor Process with Oxygen

EXAMPLE 2

Preparation of Methane Sulfonic Acid (MSA) from Dimethyl Disulfide (DMDS)

To the round bottom flask of Example 1 was added 8 g. of 48% HBr (0.048 moles), 13 g. $H_2O$ and 0.5 g. of 68% $HNO_3$. A solution of 0.5 g. of 68% $HNO_3$ in 13 g. of $H_2O$ was placed in one of the addition funnels. To another addition funnel 18.8 g. (0.2 moles) of dimethyl disulfide (DMDS) was added. The system was first purged with oxygen to remove air and then five drops of DMDS were added and oxygen bubbled into the reaction flask, as described above. A heat gun was used to heat and initiate the reaction which took about ten minutes. When the reaction started, a white gaseous mist formed, which turned a light brown color. At this point, an additional amount of DMDS was added and this caused fresh white mist to form and change to brown. These additions of DMDS were repeated throughout the course of the experiment. As the reaction proceeded, the rate slowed down and, to accelerate the reaction rate, the nitric acid-water solution was added at a rate to prevent excessive movement of the scrubbing fluid in the scrubbing flasks in either direction.

About half-way through the DMDS addition, it was necessary to add an additional solution of 0.5 g. $HNO_3$ in 13 g. of $H_2O$ to the reaction mass to maintain the rate of reaction. At the end of the reaction, an additional 0.54 g. of 68% $HNO_3$ was added in two portions. After the addition of all the chemicals was complete, the reaction flask was heated to about 60° C. to about 70° C. until a clear brown solution was obtained and at this point, the oxygen feeding tube was disconnected. The total weight of liquid starting materials added was 67.8 g. The total weight of reaction mixture recovered was 81 g., a net gain of 13.2 g., resulting from the absorption and oxygen (82.5% of theoretical). The total amount of $HNO_3$ used was 5.5% of the weight of DMDS reacted and the amount of HBr used was 20% of DMDS.

The 81 g. of the reaction mixture recovered was mixed with about 50 g. of water and heated in a flask on a hot plate to strip off the volatile materials. When the boiling point of the residual liquid reached 140° C., the stripping was terminated. The contents of the flask weighed 48.5 g., and had a specific gravity of 1.36, indicating a 87% yield of methane sulfonic acid. Titration of the aqueous product solution with a standardized base showed the MSA content to be 69%.

EXAMPLE 3

Preparation of Methane Sulfonic Acid MSA from DMDS

To a round bottom flask of the apparatus described in Example 1 was added 13.3 g. of $H_2O$, 2 g. of 48% HBr and 1 g. of 68% $HNO_3$. In one addition funnel was placed 2 g. of $HNO_3$ in 13.5 g. of $H_2O$, and in another addition funnel, 18.8 g. of DMDS (0.2 moles). The reaction was carried out with oxygen addition in a similar manner to that described in Example 1, but at the end of the reaction no further addition of $HNO_3$ was made so that 13.2 g. of the aqueous HNO$_3$ was not used. The total material added to the reaction was 18.8 g. (0.2 moles) of DMDS, 2 g. of 48% HBr (5.1% of DMDS), 2.3 g. of 68% HNO$_3$ (8.3% of DMDS), and 22 g. of H$_2$O to give 45.1 g. of total material in the reaction flask. At the end of the reaction, 60.5 g. of the reactant mixture was recovered which represents a net weight increase of 15.4 g. from O$_2$ absorption (96% of theoretical). The crude reaction mixture was boiled three times with three portions of 40 g. of water in a flask to strip off volatiles. The stripping was terminated at 143° C. to yield a total of 50.9 g. of product, having a specific gravity. of 1.37 and containing 72.4% MSA. The yield of MSA recovered was 96%.

EXAMPLE 4

Preparation of Ethane Sulfonic Acid (ESA) from Diethyl Disulfide (DEDS)

To the round bottom flask of Example 1 was added 1 g. of 68% HNO$_3$, 6 g. of HBr and 20.2 g. of H$_2$O. After purging with O$_2$, five drops of 12.2 g. (0.1 moles) diethyl disulfide (DEDS) was added from the addition funnel and oxygen was bubbled through the reaction mass. The reaction mass was heated to about 65° C. to initiate the reaction. The flask was heated at low heat through the entire course of the reaction. After about one hour, the reaction slowed down and additional portions of 0.05 g. and 0.07 g. of 68% HNO$_3$ were added to maintain the reaction rate. The reaction was completed in one hour and 45 minutes. The color of the reaction mixture was a deep brownish red. An additional 2.16 g. (0.018 moles) of HNO$_3$ was added and when the solution turned into a clear, deep brownish red, the reaction was terminated. The total time elapsed was two hours and 20 minutes. The HNO$_3$ used was 18.3% of DEDS and the HBr used was 23.6% of DEDS.

A total of 50.38 g. of crude ethane sulfonic acid product reaction mixture was recovered which represents an increase of 8.68 g. from O$_2$ absorption (91.9% of theoretical).

The crude product was mixed with 52 g. of water and boiled to strip off volatiles. The stripping was stopped when the liquid temperature reached 140° C. 32.24 g. of material was recovered. There was no detectable amount of HNO$_3$ in the product and product purity was 74.8%. The yield based on ESA recovered was 91.8%.

EXAMPLE 5

Preparation of Methane Sulfonyl Chloride (MSC) from DMDS

The apparatus described in Example 1 was used, except that the round bottom flask was cooled with a cold water bath.

In the round bottom reaction flask was placed 62.15 g. of 31% HCl solution (0.52 moles), 1.1 g. of 68% HNO$_3$ and 5.15 g. of 48% HBr. In one addition funnel was placed 2.05 g. of 68% HNO$_3$ and in another was placed 18.8 g. of DMDS (0.2 moles). The amount of HNO$_3$ used was 7.4% by weight of DMDS and the HBr used was 13% of DMDS. The addition of the reagents was in the same manner as described in Example 1 and the reaction temperature was held between 0° C. and 50° C. After one hour and 55 minutes, the reaction was terminated. The heavy, bottom, oily organic layer was separated from the light aqueous layer and 21.3 g. (46.5% yield) of heavy liquid MSC product (Sp. Gr. 1.48) was obtained.

EXAMPLE 6

This example, without the use of HBr or Br$_2$, illustrates the importance of Br$_2$ or HBr in the process of this invention.

The same apparatus described in Example 1 was used. The round bottom flask was charged with 13.5 g. of water and 1.02 g. of 68% HNO$_3$. One addition funnel was charged with 18.8 g. of dimethyl disulfide (DMDS) (0.2 moles) and the other charged with 2 g. of 68% HNO$_3$ and 13.5 g. of water. Five drops of the DMDS were then dropped into the round bottom flask from the addition funnel. The reaction mass was heated to about 60° C. to initiate the reaction. After about 12 minutes, a gaseous white cloud appeared which quickly turned light brown in color. This is a typical reaction and was observed in all four previous examples. More DMDS was added when the color turned clear brown in the gas phase. This color change occurred about every one to one and a half minutes as the DMDS was added. After about 40 minutes, the reaction rate began to slow down and the aqueous HNO$_3$ in the other addition funnel was then added at a rate of ten drops per addition. The rate of reaction increased after HNO$_3$ was first added, but the reaction rate decreased after 65 minutes and came to a stop after 75 minutes. At this point, the oxygen absorption essentially stopped, even with accelerated addition of HNO$_3$. The total addition of HNO$_3$ was completed after 82 minutes from the reaction start. The reaction mass was then held for another one-half hour under mild heating. No additional oxygen absorption was observed during this time period. The reaction was terminated and allowed to stand. This caused three layers to be formed, none of which contained any significant amount of the MSA product.

EXAMPLE 7

Preparation of Dodecane Sulfonic Acid from Dodecanethiol (DDSH)

The reaction apparatus described in Example 1 was used. To the round bottom flask was added 1.0 g. of 68% HNO$_3$, 2 g. of 48% HBr and 10 g. of water. One addition funnel was charged with 20.2 g. (0.1 moles) of dodecanethiol (DDSH), and in the other addition funnel was placed 1.5 g. of 68% HNO$_3$ in 10.0 g. of water. The reactor system was purged with oxygen before seven drops of DDSH were added. The reaction mass was heated from about 65° C. to about 75° C. and held at this temperature range during the entire process. After about 15 minutes, the reaction started and foam formed in the flask which increased in volume as reaction proceeded. The addition of DDSH, oxygen and HNO$_3$, solution was carried out so that the reaction rate was under control as discussed above. After one hour and 15 minutes, it was necessary to add an additional 10 g. of water to the round bottom flask to enable the reaction mixture to be stirred. The reaction was completed after 3 hours and 10 minutes and, upon cooling, 46.3 g. of a white semisolid mass with a consistency of cream cheese was obtained. There were 10.1 g. of HNO$_3$ solution left in the addition funnel. Because of the foaming tendency, there was no attempt to steam-strip the product to effect separation. The product was analyzed by titration and found to contain a total of 0.069 equivalents of acidity.

Assuming that the added amounts of nitric acid (0.013 equivalents, 4.04% of DDSH) and HBr (0.012 equivalents, 4.8% of DDSH) remained unreacted, the acidity contributed by the product dodecane sulfonic acid was 0.044 equivalents, representing a 44% yield.

IIB. Two Reactor Process Using Oxygen

EXAMPLE 8

Preparation of MSA from Methyl Mercaptan

A two reactor system was used. The first reactor was a 100-ml round bottom flask equipped with an oxygen gas injection device, a liquid returning port, an off-gas outlet, a sidearm near the bottom for liquid discharge, a magnetic stirrer, and a thermometer. The second reactor was a 50-ml round bottom flask equipped with a gas injection device, a liquid intake port, a thermometer, and a sidearm for liquid discharge. The sidearm of the first reactor was connected to the liquid intake port of the second reactor with plastic tubing. A pump connecting the discharge sidearm of the second reactor and the liquid returning port of the first reactor was used for the circulation of the reaction fluid. The off-gas outlet was connected to a scrubber.

The scrubber consisted of two 250-ml Erlenmeyer flasks connected in series and filled with a scrubbing fluid, such as nitric acid or hydrogen peroxide solution.

The first reactor was charged with 45 g. of a 48% HBr solution, 106 g. of $H_2O$ and 2.4 g. of 67% $HNO_3$. The reactor was heated to 70° C. to initiate the initial bromine generation. When the liquid turned brown, the discharge outlet was opened to deliver the bromine containing mixture to the second reactor by gravity, until the gas delivery device was submerged. Both reactors were agitated by a magnetic stirrer. Then, delivery of oxygen and methyl mercaptan gases to the first and second reactors, respectively, was commenced. At the same time, the circulating pump was turned on to begin the circulation of the reaction fluid. The rate of oxygen delivery was maintained such that no off-gas bubbled through the scrubber. The rate of methyl mercaptan delivery was maintained such that the reaction mixture in the second reactor remained brown for the entire reaction period. As the reaction started, the temperature rose to about 90° C. The rate of heating was then decreased, to maintain a temperature around 75° C.

After 14 hours of reaction time, 71 g. of the reaction mixture were withdrawn for separating the methane sulfonic acid by distillation. The residue, boiling at 138° C. and weighing 13 g., contained 68% methane sulfonic acid. A semi-quantitative barium sulfate precipitation test showed a sulfuric acid content of less than 240 ppm.

EXAMPLE 9

Preparation of MSA from Methyl Mercaptan

The apparatus and procedure were similar to that of Example 8, except in that the rate of methyl mercaptan addition was higher. From time to time, the reaction mixture in the second reactor became pale yellow. At the beginning of the procedure, 50 g. of $H_2O$, 50 g. of 48% HBr and 2 g. of 67% $HNO_3$ were charged to the first reactor. After 7 hours of reaction time, a total of 128 g. of reaction mixture was recovered. After distilling off the low-boiling components, 20 g. of 72% methane sulfonic acid was recovered. The sulfuric acid content was greater than 240 ppm., but was less than 540 ppm.

III. Nitric Acid as a Bromine Generating Agent

Two different assemblies are interchangeably used for this process: either a one-reactor system, or a two-reactor system. Both systems used the same nitric acid regeneration device. This device was made of a 500-ml filtering flask fitted with inlet tubing capable of reaching down to the bottom of the flask. A three-way tee was connected to the inlet and an oxygen source. The sidearm of the flask was used as a gas outlet, and was connected to the scrubber described earlier.

A. One-reactor System

This system consisted of a flask equipped with a pressure equalizing addition funnel; a gas injection device; a thermometer; an off-gas outlet; and a magnetic stirrer. The off-gas outlet was connected to the three-way tee of a nitric acid regeneration system.

EXAMPLE 10

Preparation of MSA from Methyl Mercaptan

This example used a 100-ml reaction flask. The reactor was charged with 50 g. of 67% $HNO_3$ and 3 g. of 48% HBr. The reactants were agitated with a magnetic stirrer. Bromine was generated on initial heating of the reactor. Methyl mercaptan was delivered into the mixture after bromine began to appear. The rate of methyl mercaptan addition was maintained such that the temperature of the reaction mixture was maintained at 90–95° C. The oxygen flow to the nitric acid regeneration system was adjusted to such a rate that there was no movement of gas into or out of the scrubber. After 1.5 hours, the mixture became light yellow. The reaction was then terminated. The 53 g of reaction mixture formed was heated at its boiling point of about 108° C. for about 2 hours to ensure the completion of the reaction. Distillation of the resulting mixture until the residue reached 145° C., yielded 30 g. of 79% methane sulfonic acid. The sulfuric acid content was more than 240 ppm., but less than 540 ppm.

EXAMPLE 11

Preparation of Ethyl Sulfonic Acid from Ethyl Mercaptan

In this example, the reactor flask was a 2000-ml three-necked flask. It was equipped with similar devices to the smaller reactor used in Example 10. A pressure-equalized addition funnel was used to add nitric acid to the reactor.

The reactor was charged with 50 g. of a 48% HBr solution and 154 g. of water. A few grams of nitric acid were dropped into the flask from the addition funnel, and heat was applied to initiate the bromine generation. The solution was agitated in the reactor. Addition of gaseous ethyl mercaptan was commenced at that time. The flow rate of ethyl mercaptan was adjusted to maintain the temperature of the reaction mixture at 90–95° C. without the use of an external heating source. The rate of oxygen flow was maintained at such rate that there was no net movement of gas in the scrubber. A continuous addition of nitric acid was also maintained to keep a dark brown color in the reaction mixture. After 5 hours and 40 minutes a total of 687 g. of 67% nitric acid had been added. The addition of ethyl mercaptan was continued until the color of the mixture started to lighten. The reaction was then terminated. It was heated at about 98° C. overnight. Upon distilling off the low boiling components, 529 g. of 73.4% ethane sulfonic acid (a 97% yield based on the $HNO_3$ used) was recovered. The sulfuric acid content was greater than 540 ppm.

B Two-reactor System

This system is a modification of the two-reactor system described for the process using oxygen in the generation of bromine. The same assembly was used, with the following modifications: the oxygen delivery device was replaced with a pressure equalizing addition funnel, and the off-gas outlet was connected to the nitric acid regeneration device.

EXAMPLE 12

Preparation of MSA from Methyl Mercaptan

The first reactor was charged with 40 g. of 48% HBr, 76 g. of water and 2 g. of 67% $HNO_3$. Heat was applied to initiate the bromine formation. The bromine-containing reaction mixture was transported to the second reactor by gravity, where methyl mercaptan was introduced. The circulation pump was activated to transport the reaction mixture from the second reactor back to the first reactor. 64 g. of nitric acid in the addition funnel was gradually added to the first reactor. The rate of flow of methyl mercaptan was adjusted such that the temperature of the second reactor was kept at about 70–75° C. After 2 hours, the addition of the 64 g. of $HNO_3$ was completed. The flow of methyl mercaptan was continued until the color of the mixture in the first reactor was light brown. 70 g. of the finished reaction mixture was recovered, which was heated at about 108° C. for about 2 hours. After evaporating off the lower boiling components, 43 g. of 72% methane sulfonic acid was obtained. The sulfuric acid content was less than 240 ppm.

The invention has been described with reference to preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A process for the preparation of alkane sulfonic acids or alkane sulfonyl chlorides of formula $R_1$—$SO_2$—Y where $R_1$ is an alkyl group of from 1 to about 18 carbon atoms and Y is —OH or —Cl, which comprises oxidizing a sulfur compound of the formula $R_1SZ$ where Z is —H or —$SR_1$, said oxidation occurring in aqueous phase with an oxygen containing gas in the presence of nitric acid or nitrogen oxides and bromine or HBr and, where a sulfonyl chloride product is desired, in the presence of HCl.

2. A process for the preparation of alkane sulfonic acids of formula $R_1$—$SO_2$—OH where $R_1$ is an alkyl group of from 1 to about 18 carbon atoms, which comprises oxidizing an alkyl sulfur compound of structure $R_1SZ$ where Z is —H or —$SR_1$, said oxidation being carried out with oxygen in aqueous phase in the presence of nitric acid and HBr or $Br_2$, the amount of each of said nitric acid and HBr or $Br_2$ being from about 0.5% to about 50% by weight of the said sulfur compound.

3. The process of claim 2 wherein methylsulfonic acid is prepared from dimethyl disulfide in the presence of from about 5% to about 25% by weight of said dimethyl disulfide of $HNO_3$ and from about 2% to about 25% by weight of said dimethyl disulfide of HBr or $Br_2$.

4. The process of claim 2 wherein ethanesulfonic acid is prepared from diethyl disulfide in the presence of from about 5% to about 25% by weight of said diethyl disulfide of $HNO_3$ and from about 2% to about 25% by weight of said diethyl disulfide of HBr or $Br_2$.

5. The process of claim 2 wherein dodecane sulfonic acid is prepared from dodecanethiol.

6. A process for the preparation of alkane sulfonyl chlorides of the formula $R_1$—$SO_2Cl$ where $R_1$ is an alkyl group of from about 1 to about 18 carbon atoms which comprises oxidizing a sulfur compound of the formula $R_1SZ$, where Z is —H or —$SR_1$, said oxidation being carried out in an aqueous phase with oxygen in the presence of nitric acid, HCl and HBr or $Br_2$.

7. The process of claim 6 wherein the amount of each of nitric acid and said HBr or $Br_2$ is from about 0.5% to about 50% by weight of said sulfur compound reactant.

8. The process of claim 7 wherein dimethyl disulfide is oxidized to methane sulfonyl chloride.

9. A process for the preparation of alkane sulfonic acids or alkane sulfonyl chlorides of a formula $R_1$—$SO_2$—Y where $R_1$ is an alkyl group of from 1 to about 18 carbon atoms and Y is —OH or —Cl, which comprises oxidizing a sulfur compound of the formula $R_1SZ$, where Z is —H or —$SR_1$, said oxidation occurring in aqueous phase in the presence of nitric acid and bromine and, where a sulfonyl chloride product is desired, in the presence of HCl.

10. The process of claim 9 wherein the bromine is generated from HBr in the presence of nitric acid or nitrogen oxides.

11. The process of claim 10, wherein the bromine is generated from HBr in the presence of oxygen and a catalytic amount of nitric acid.

12. The process of claim 10 wherein the bromine is initially generated from HBr in the absence of the sulfur compound.

13. The process of claim 9 wherein an excess of bromine is maintained while the sulfur compound is present.

14. The process of claim 9 wherein the nitric acid is generated from a nitrogen oxide and oxygen in the absence of the sulfur compound.

15. The process of claim 10 wherein the process comprises two steps:

the first step comprising the oxidation of HBr to bromine in the presence of nitric acid or a nitrogen oxide and in the absence of the sulfur compound, and the second step comprising the oxidation of the sulfur compound in the presence of the bromine.

16. The process of claim 15 wherein the first step further comprises the oxidation of HBr in the presence of an oxygen containing gas.

17. The process of claim 15 wherein the second step is substantially free of oxygen.

18. The process of claim 15 wherein the first and second steps are repeated sequentially, each of the repeated first steps providing for regeneration of bromine from HBr that is formed in the second step, and each of the repeated second steps providing for the oxidation of an additional amount of the sulfur compound.

19. The process of claim 15, wherein the HBr and the nitric acid are reacted in a first reactor to form a mixture containing the bromine, the mixture being transported to a second reactor where the sulfur compound is oxidized to an alkane sulfonic acid.

20. The process of claim 19, wherein the sulfur compound is added to the second reactor at a controlled rate, whereby substantially all the sulfur compound reactant is oxidized to the alkane sulfonic acid.

21. The process of claim 19, wherein the mixture containing an alkane sulfonic acid is returned to the first reactor for bromine regeneration then transported to the second reactor where additional sulfur compound reactant is oxidized to the alkane sulfonic acid.

22. The process of claim 19 wherein a methyl sulfonic acid-containing product is prepared from methyl mercaptan and wherein sulfuric acid is present in the product at a concentration of 300 ppm., or less.

* * * * *